United States Patent [19]

Campbell et al.

[11] 4,178,305

[45] Dec. 11, 1979

[54] OXIDATIVE DEHYDROGENATION OF PROPIONITRILE TO ACRYLONITRILE

[75] Inventors: Charles R. Campbell; William A. Heckle; Marion J. Mathews, all of Pensacola, Fla.

[73] Assignee: Monsanto Company, St. Louis, Mo.

[21] Appl. No.: 953,984

[22] Filed: Oct. 23, 1978

Related U.S. Application Data

[63] Continuation-in-part of Ser. No. 857,835, Dec. 5, 1977, abandoned, and a continuation-in-part of Ser. No. 732,556, Oct. 15, 1976, abandoned.

[51] Int. Cl.$^2$ .................. C07C 120/00; C07C 121/32
[52] U.S. Cl. .................................................. 260/465.9
[58] Field of Search ............................... 260/465.9

[56] References Cited

U.S. PATENT DOCUMENTS

| | | | |
|---|---|---|---|
| 3,207,806 | 9/1965 | Bajars | 260/465.9 X |
| 3,308,198 | 3/1967 | Bajars | 260/465.9 X |
| 3,520,915 | 7/1970 | Kominami et al. | 260/465.9 |

*Primary Examiner*—Joseph Paul Brust
*Attorney, Agent, or Firm*—Thomas Y. Awalt, Jr.

[57] ABSTRACT

Propionitrile is subject to oxidative dehydrogenation at high temperatures in the presence of a stoichiometric excess of a metal oxide oxygen donor to produce acrylonitrile at a high rate of conversion and selectivity.

6 Claims, No Drawings

OXIDATIVE DEHYDROGENATION OF PROPIONITRILE TO ACRYLONITRILE

CROSS REFERENCES TO RELATED APPLICATIONS

This application is a continuation-in-part of our application Ser. No. 732,556 filed Oct. 15, 1976 (now abandoned), and co-pending application Ser. No. 857,835, filed Dec. 5, 1977 (now abandoned).

BACKGROUND OF THE INVENTION

A. Field of the Invention

The invention relates to the production of acrylonitrile from propionitrile.

B. The Prior Art

A long standing problem in the manufacturing of adiponitrile from acrylonitrile has been the loss of adiponitrile by way of conversion to the by-product propionitrile, which, in a typical electrohydrodimerization reaction, occurs at a rate of about 4–7 mole % of the acrylonitrile employed as a starting material.

One attempt made to reconvert propionitrile to acrylonitrile involved a low temperature gas phase catalytic dehydrogenation in the presence of stannous oxide. According to U.S. Pat. No. 3,520,915, one-pass propionitrile conversions of 15–25%, with selectivities to acrylonitrile of 80–90%, are attained at temperatures of 500°–600° C. with unspecified but comparable yields theorized at 300°–700° C. Conversion rates of this order of magnitude are obviously suitable for commercial application only where a series of repeat passes can be employed.

A dehydrogenation reaction for propionitrile in which high acrylonitrile selectivity is maintained in conjunction with a commercially acceptable propionitrile conversion would be a significant advance in the art and is an object of this invention.

SUMMARY OF THE INVENTION

Propionitrile is oxidatively dehydrogenated to form acrylonitrile in the presence of an excess of at least about 15% of a metal oxide donor over the amount of the metal oxide stoichiometrically required to furnish the oxygen necessary for the oxidative reaction at temperatures of 725°–900° C. The metal oxide donor is selected from the group consisting of stannic oxide, lead oxide, zinc oxide and antimony oxide. Stannic oxide is preferred, and it is preferably supported on an alumina carrier. Feed rate is adjusted so as to provide, with respect with the particular apparatus, the best conversion rate of propionitrile, without sacrifice of an acceptable selectivity rate of acrylonitrile.

DETAILED DESCRIPTION OF THE INVENTION

In the process of this invention propionitrile is converted to acrylonitrile by subjecting the propionitrile to temperatures of about 725°–900° C. in the presence of a 15% stoichiometric excess of a metal oxide donor. This results in a primarily oxidative (as opposed to a primarily catalytic) dehydrogenation reaction which affords surprisingly higher yields of the acrylonitrile and higher conversion rates of propionitrile. To obtain the advantages of this invention, it is essential that the reaction be conducted at the specified temperature of about 725°–900° C., preferably 725°–800° C., to thereby avoid a primarily catalytic dehydrogenation which ordinarily occurs at lower temperatures.

It is also essential to use a stoichiometric excess of at least about 15% by weight of the metal oxide required to furnish the oxygen necessary for oxidative dehydrogenation of the propionitrile in order to avoid the primarily catalytic dehydrogenation. Any metal oxide oxygen donor may be employed which readily yields oxygen and which does not react unfavorably with propionitrile. We have found that stannic oxide is especially preferred as an oxygen donor. Lead oxide, zinc oxide and antimony oxide are useful but somewhat less selective in conversion of propionitrile to acrylonitrile. The oxide may be separately prepared by conventional methods or it may be prepared in situ, if desired, by passing air over the heated or molton metal.

For the purposes of convenience and as a possibly useful supplemental source of oxygen for the reaction, it is preferable but not essential to support the oxygen donor on a carrier containing oxygen such as alumina. Since the ability to furnish oxygen as a supplemental donor is not essential, any carrier which does not otherwise interfere with or poison the reaction may be employed. Conventional immersion methods are used to prepare the supported catalyst. Any oxygen lost by the carrier or the donor during the reaction may be replaced simply by passing air or any oxygen-containing gas over the used carrier after completion of the reaction or reaction series.

Propionitrile (PN) may be employed as feedstock in any relatively pure form which does not contain material deleterious to the reaction or the metal oxide. Percent of purity is not critical. It is preferably diluted with an inert gas such as nitrogen, or a relatively inert non-interferring (to the reaction) diluent such as steam. The feestock, pure or diluted, is preferably vaporized prior to being fed into the reactor; but it may be fed in liquid form into the reactor thereafter to be vaporized. The amount of propionitrile employed is limited by the amount of the oxygen donor present and the rate of feed is adjusted, according to the particular apparatus, for maximum conversion of the propionitrile.

EXAMPLE 1 (preparation of supported oxygen donor)

113.0 g of Norton SA5405 alumina (5–14 mesh) was placed in a 1-liter flask and this attached to a rotary evaporator. Reduced pressure was applied to the rotary evaporator and the flask was rotated and warmed at 70°–80° C. by means of a water bath. Then 50 g $SnO_2$ (T-148, Fisher Scientific) was slurried with 200 ml of water and added to the alumina support through the rotary evaporator liquid addition system. After the water had been removed under vacuum, the solids were put in a muffle furnace at 550° C. for 2 hours. 162.6 g of oxygen carrier having 30.5 weight % $SnO_2$ on alumina was recovered. [0.4 g $SnO_2$ adhered to the side of the 1-liter flask.]

EXAMPLE 2 (preparation of supported oxygen donor)

88.7 g Norton SA5405 alumina (5–8 mesh) was placed in a 1-liter flask and this attached to a rotary evaporator. Reduced pressure was applied to the rotary evaporator and the flask warmed to 70°–80° C. by means of a water bath. Then 40 g of $SnO_2$ (T-148, Fisher Scientific) slurried in 150 ml water was added to the alumina support through the rotary evaporator liquid addition system and the mixture warmed and rotated until the water had been removed. The solids were then heated in a muffle furnace at 500° C. for 2 hours. The solids now weighted 127.3 g indicating 1.4 g of SnO$_2$ was lost by adherence to the sides of the flask during evaporation of the water. The solids were again put in a 1-liter flask attached to a rotary evaporator and another 40 g stannic oxide slurried in 150 ml water was added to the solids through the rotary evaporator addition system. The mixture was warmed and rotated until the water had been removed. The solids were placed in a muffle furnace at 500° C. for 2 hours and 166.0 g of oxygen carrier (45.7 mole % SnO$_2$) was recovered.

EXAMPLE 3 (comparative example)

134.4 g (80 cc) of the 30.5% SnO$_2$ on alumina oxygen carrier prepared as described in Example 1 was placed in a quartz glass tubular reactor having a 15 mm ID. and a fritted glass support plate at the bottom of the reaction zone. The reaction zone was heated to 650° C. and 21.6 ml PN/hr and 11.0 l N$_2$/hr (GHSV-755 hr$^{-1}$) were passed over the oxygen carrier for 8.3 minutes. On one pass 23.3 mole % of PN was converted with a selectivity of AN at 81.9 mole % (0.191 moles of AN per mole of PN fed into the reaction zone).

EXAMPLE 4 (comparative example)

After regenerating the SnO$_2$ on alumina oxygen carrier from Example 3 with air, the reactor temperature was adjusted to 650° C. and 7.74 ml PN/hr and 3.0 l N$_2$/hr (GHSV-231 hr$^{-1}$) were passed over the oxygen carrier for 23.3 minutes, resulting in a 37.1 mole % PN conversion and a 66.2 mole % AN selectivity (0.245 moles of AN per mole of PN).

EXAMPLE 5

After regenerating the SnO$_2$ on alumina oxygen carrier from Example 4, the reactor temperature was adjusted to 750° C. and 21.9 ml PN/hr and 15.0 l N$_2$/hr (GHSV-1029 hr$^{-1}$) were passed through the reactor for 8.2 minutes, resulting in an 85.4 mole % PN conversion and a 67.6 mole % AN selectivity (0.58 moles of AN per mole of PN).

EXAMPLE 6

65.5 g (40 ml) of the 45.7% SnO$_2$ or alumina oxygen carrier described in Example 2 was placed in the reactor described in Example 3 and brought to 760° C. 48.5 ml PN/hr (GHSV-1457 hr$^{-1}$) was passed over the oxygen carrier for 9.5 minutes, resulting in a 73.6 mole % PN conversion and a 56.1 mole % AN selectivity (0.41 moles of AN per mole of PN).

EXAMPLE 7

After air regenerating the oxygen carrier described in Example 6 at 760° C., 27.7 ml PN/hr and 6.7 l N$_2$/hr (GHSV-1468 hr$^{-1}$) were passed over the carrier at 760° C. for 16.9 minutes, resulting in an 81.8 mole % PN conversion and a 59.7 mole % AN selectivity (0.49 moles of AN per mole of PN).

EXAMPLE 8

After air regenerating the oxygen carrier from Example 7 at 755° C., 13.2 ml PN/hr and 10.8 l N$_2$/hr (GHSV-1407 hr$^{-1}$) were passed over the oxyen carrier at 755° C. for 32.1 minutes resulting in an 87 mole % PN conversion and a 68.3 mole % AN selectivity (0.59 moles of AN per mole of PN).

Examples 5, 7 and 8 demonstrate an increase in PN conversion and AN selectivity with addition of a diluent to the PN feed.

We claim:

1. A primarily oxidative process for dehydrogenation of propionitrile to acrylonitrile comprising subjecting propionitrile to a temperature of about 725°–900° C. in a reaction medium consisting essentially of the propionitrile, a metal oxide oxygen donor, and an alumina carrier, the metal oxide being present in an excess of about 15% by weight of the metal oxide required to furnish the oxygen necessary for oxidative dehydrogenation of a propionitrile, the metal oxide oxygen donor being selected from the group consisting of stannic oxide, lead oxide, zinc oxide and antimony oxide.

2. The process of claim 1 wherein the oxidative dehydrogenation is conducted at a temperature of 725°–800° C.

3. The process of claim 1 wherein the metal oxide is stannic oxide.

4. The process of claim 3 wherein the oxidative dehydrogenation is conducted at a temperature of about 750° C.

5. The process of claim 3 wherein the stoichiometric excess of the stannic oxide is 30–50%.

6. The process of claim 1 conducted successively with regeneration of the donor upon depletion of oxygen content being achieved by passing an oxygen-containing gas over the donor.

* * * * *